(12) United States Patent
Laengle

(10) Patent No.: US 9,366,637 B2
(45) Date of Patent: Jun. 14, 2016

(54) METHOD FOR ESTABLISHING DISTORTION PROPERTIES OF AN OPTICAL SYSTEM IN A MICROLITHOGRAPHIC MEASUREMENT SYSTEM

(71) Applicant: Carl Zeiss SMS GmbH, Jena (DE)

(72) Inventor: Mario Laengle, Jena (DE)

(73) Assignee: Carl Zeiss SMS GmbH, Jena (DE)

( * ) Notice: Subject to any disclaimer, the term of this patent is extended or adjusted under 35 U.S.C. 154(b) by 65 days.

(21) Appl. No.: 14/307,276

(22) Filed: Jun. 17, 2014

(65) Prior Publication Data

US 2014/0369592 A1 Dec. 18, 2014

(30) Foreign Application Priority Data

Jun. 18, 2013 (DE) .......................... 10 2013 106 320

(51) Int. Cl.
| | |
|---|---|
| *G06K 9/36* | (2006.01) |
| *G01N 21/84* | (2006.01) |
| *G01N 21/95* | (2006.01) |
| *G06T 7/00* | (2006.01) |
| *G01M 11/02* | (2006.01) |
| *G03F 7/20* | (2006.01) |
| *G01N 21/956* | (2006.01) |

(52) U.S. Cl.
CPC ............ *G01N 21/84* (2013.01); *G01M 11/0257* (2013.01); *G01N 21/95* (2013.01); *G03F 7/706* (2013.01); *G03F 7/70591* (2013.01); *G06T 7/0004* (2013.01); *G06T 7/0018* (2013.01); *G01N 2021/95676* (2013.01); *G06T 2207/30148* (2013.01); *G06T 2207/30168* (2013.01)

(58) Field of Classification Search
None
See application file for complete search history.

(56) References Cited

U.S. PATENT DOCUMENTS

| | | | |
|---|---|---|---|
| 6,534,500 B2 | 3/2003 | D'Alche-Biree | |
| 8,260,033 B2 | 9/2012 | Arnz et al. | |
| 8,416,412 B2 | 4/2013 | Schellhorn et al. | |
| 8,717,581 B2 | 5/2014 | Laengle | |
| 2003/0091913 A1* | 5/2003 | Shiode ................... | G03F 7/706 430/22 |
| 2009/0225293 A1* | 9/2009 | Shigenobu ............. | G03B 27/32 355/53 |
| 2010/0097608 A1 | 4/2010 | Schellhorn et al. | |

(Continued)

FOREIGN PATENT DOCUMENTS

| | | | |
|---|---|---|---|
| DE | 102006059431 | 6/2008 | ................ G03F 7/20 |
| DE | 102007033815 | 11/2008 | ................ G03F 9/00 |

(Continued)

OTHER PUBLICATIONS

M. Längle et al.: "Pattern placement metrology using PROVE high precision optics combined with advanced correction algorithms," Proc. SPIE 8082, 80820J (2011).

(Continued)

*Primary Examiner* — Brian P Werner
(74) *Attorney, Agent, or Firm* — Fish & Richardson P.C.

(57) ABSTRACT

A method for establishing distortion properties of an optical system in a microlithographic measurement system is provided. The optical system has at least one pupil plane, in which the distortion properties of the optical system are established on the basis of measuring at least one distortion pattern, which the optical system generates when imaging a predetermined structure in an image field. The distortion properties of the optical system are established on the basis of a plurality of measurements of distortion patterns, in which these measurements differ from one another in respect of the intensity distribution present in each case in the pupil plane.

14 Claims, 4 Drawing Sheets

(56) References Cited

U.S. PATENT DOCUMENTS

| | | |
|---|---|---|
| 2010/0104128 A1 | 4/2010 | Arnz et al. |
| 2012/0063666 A1 | 3/2012 | Arnz et al. |

FOREIGN PATENT DOCUMENTS

| | | | | |
|---|---|---|---|---|
| DE | 102010047051 | 3/2012 | ................ | G06T 7/60 |
| DE | 102011086949 | 5/2013 | ................ | G03F 7/20 |
| DE | 10 2013 101 445 | 8/2014 | ............ | G01M 11/02 |
| DE | 10 2013 107 976 | 1/2015 | ............. | G01B 11/03 |
| WO | WO 01/12265 | 2/2001 | ............. | A61P 25/30 |
| WO | WO 2013/075930 | 5/2013 | ................ | G03F 7/20 |
| WO | WO 2014/125000 | 8/2014 | ................ | G03F 1/84 |

OTHER PUBLICATIONS

Office Action from the German Patent and Trademark Office, Application No. DE 10 2013 106 320.9 dated Jun. 12, 2014 (5 pages).

* cited by examiner

METHOD FOR ESTABLISHING DISTORTION PROPERTIES OF AN OPTICAL SYSTEM IN A MICROLITHOGRAPHIC MEASUREMENT SYSTEM

CROSS REFERENCE TO RELATED APPLICATION

This application claims priority to German patent application 10 2013 106 320.9, filed on Jun. 18, 2013. The above application is incorporated by reference.

TECHNICAL FIELD

The invention relates to a method for establishing distortion properties of an optical system in a microlithographic measurement system.

BACKGROUND

Microlithography is used for producing microstructured components, such as, for example, integrated circuits or liquid crystal displays (LCDs). The microlithography process is carried out in a so-called projection exposure apparatus comprising an illumination device and a projection lens. In this case, the image of a mask (also referred to as a reticle) illuminated by the illumination device is projected, by the projection lens, onto a substrate (e.g., a silicon wafer) coated with a light-sensitive layer (photoresist) and arranged in the image plane of the projection lens, in order to transfer the mask structure to the light-sensitive coating of the substrate.

A characterization of the structures on the mask is performed both in respect of present deviations of the respective structure on the mask from the intended position predefined by the design (so-called positioning error or "registration error") and in respect of the line width of the structures ("critical dimension" (CD)).

For determining the positioning error, various methods are known in the prior art. By way of example, a "threshold-based" image evaluation can be applied to the structures of the aerial image, as is known from US 2012/0063666 A1. Alternatively, by use of a position measurement system, a first aerial image of a segment of the mask can be recorded and compared with a simulated second aerial image, whereupon the positioning error is then equated with the distance between the structures to be measured in the measured first aerial image and the simulated second aerial image.

One problem that occurs in practice, however, is that the measurement image is deformed or distorted on account of the properties of the optical system (that is to say that a coordinate grid is not exactly at right angles on the measurement image), whereas the simulated image as an ideal simulated grid does not have this property.

One known approach for taking account of the distortion consists in the latter being calibrated or "extracted computationally," i.e., the distortion being determined metrologically by a targeted measurement with test structures in the image field. In this case, however, the further problem occurs that the distortion taken as a basis in such a calibration is dependent both on the pupil illumination specifically used within the imaging optical unit of the position measurement system and on the type of structure used for calibration. In so doing, here and in the following text, "pupil illumination" is understood to mean the intensity distribution obtained in a pupil plane within the imaging optical unit of the position measurement system, in which the imaging optical unit images light coming from the mask onto a detector unit.

The distortion underlying the above-described calibration is no longer exactly valid for any other possible structures, in which the resulting structure-dependent and illumination-dependent differences in the distortion on which the calibration is based are measurable in the sub-nanometer range and may be significant.

With regard to the prior art, reference is made for example to WO 2001/012265 A1, DE 10 2007 033 815 A1 and DE 10 2006 059 431 A1, US 2010/0104128 A1, DE 10 2007 033 815 A1 and also the publication M. Längle et al.: "Pattern placement metrology using PROVE high precision optics combined with advanced correction algorithms," Proc. SPIE 8082, 80820J (2011).

SUMMARY

In a general aspect, a method for establishing distortion properties of an optical system in a microlithographic measurement system is provided. The system enables a more accurate specification of the distortion properties. The optical system has at least one pupil plane, in which the distortion properties of the optical system are established on the basis of measuring at least one distortion pattern, which the optical system generates when imaging a predetermined structure in an image field. The distortion properties of the optical system are established on the basis of a plurality of measurements of distortion patterns, in which these measurements differ from one another in respect of the intensity distribution present in each case in the pupil plane.

Initially, the invention proceeds from the consideration that the distortion occurring when measuring at least one structure in the generated image field depends on the pupil illumination specifically used in the imaging optical unit of the position measurement system such that the measurement images recorded with the position measurement system are also to be processed taking into account the distortion respectively emerging for this specific pupil illumination.

Proceeding from this consideration, the invention is based upon the concept of, in particular, establishing the distortion properties of the optical system on the basis of a plurality of measurements of distortion patterns having different pupil illuminations (i.e., different intensity distributions in the pupil plane). In particular, the invention contains the concept of carrying out a distortion correction using a suitable distortion function when processing the measurement images, which distortion function describes the dependence of the distortion on the pupil illumination such that the specific pupil illumination used in the specific case when recording the relevant measurement image can also be taken into account in respect of the influence thereof on the distortion.

In accordance with one embodiment, during the plurality of measurements of distortion patterns, only one segment from a plurality of segments is illuminated in each case in the pupil plane.

In accordance with one embodiment, a measurement image or one or more relevant portions thereof, recorded by the optical system is corrected on the basis of the established distortion properties of the optical system.

In accordance with one embodiment, the corrected measurement image is used for establishing registration errors and/or structure widths on a mask.

The corrected measurement image can be used in different ways and by means of methods respectively known per se for, e.g., establishing registration errors. In accordance with one application example, the corrected measurement image can be used in an image comparison with a simulated image (such that, in other words, in an image comparison between a measurement image and a simulated image, these images are aligned with respect to distortion effects on the basis of the established distortion properties of the optical system).

In further applications of the invention, the evaluation of the corrected measurement images for establishing registration errors can also be brought about by other methods, in which the actual position of the structure on the mask is established in each case. By way of example, a symmetry correlation as described in DE 10 2010 047 051 A1 can be carried out to this end, in which at least one symmetry operation (e.g., a point reflection or mirroring in a reference mirror plane) is carried out for a provided image comprising the structure to be established. Alternatively, it is also possible for edge detection to be carried out in the corrected measurement image, in which the position of the structure is established from the detected edge positions. In the two methods mentioned last, the registration error then emerges as difference between the actually established position and the intended position of the structure.

In particular, the distortion function ultimately to be used when processing or correcting the recorded measurement image can be established by virtue of a plurality of individual distortion functions being established initially, of which each is assigned to an (as it were "elementary") pupil illumination. Then, depending on the extent to which this specific pupil illumination corresponds to the elementary pupil illuminations, the distortion function to be used for the respectively current or specific pupil illumination when processing the measurement images recorded with the position measurement system can be calculated as a weighted sum of the individual distortion functions.

Therefore, in accordance with one embodiment, the method in particular includes the following steps:
establishing a distortion function $(V_i(x, y), i=1, \ldots, n))$ in each case for a plurality (n) of segments in the pupil plane, which distortion function specifies the distortion generated by the optical system in an image plane when illuminating the respective segment; and
calculating an overall distortion function $(V_{tot}(x, y))$ for a given intensity distribution in the pupil plane as $$V_{tot}(x, y) = \sum_{i=1}^{n} w_i \cdot V_i(x, y)$$

where $$w_i = \frac{I_i}{I_{tot}}$$

denotes a weighting factor assigned to the i-th segment in the pupil plane and $I_i$ denotes the intensity in the i-th segment for the given intensity distribution.

The plurality of individual distortion functions can be established in such a way that a portion of the pupil plane within the imaging optical unit, i.e., in each case a "pupil segment," is assigned in each case to each of these individual distortion functions. When establishing the distortion function ultimately to be used when processing the recorded measurement images, the individual distortion functions are thereupon taken into account to the extent to which the relevant "pupil segment" contributes to the actually employed pupil illumination or the specific illumination setting.

The optical system according to the invention can, in particular, be equipment for determining the position of structures on a microlithographic mask, an inspection measurement system for measuring defects of photomasks, equipment for determining the line width in photomasks, a phase measurement system for photomasks or inspection equipment for localizing defects of photomasks.

Further embodiments of the invention can be gathered from the description and the dependent claims.

The invention is explained in more detail below on the basis of exemplary embodiments depicted in the attached drawings.

DETAILED DESCRIPTION

Figure 1:
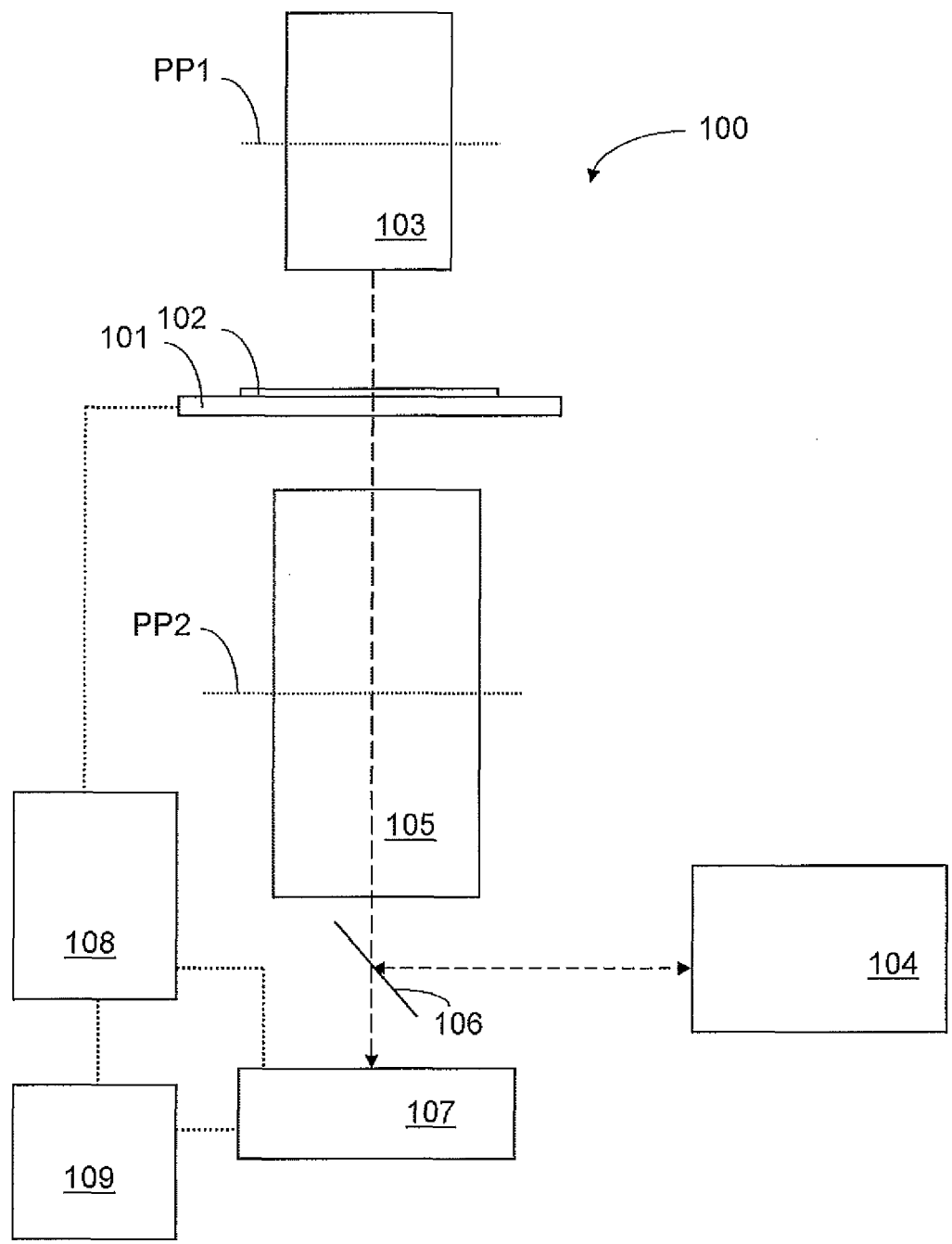
FIG. 1 shows a schematic illustration for explaining an exemplary design of a position measurement system which can be used in the method according to the invention.

FIG. 1 shows a possible design of a position measurement system 100, in which the present invention can be realized.

In accordance with FIG. 1, a mask 102 is mounted on a platform 101 displaceable in three spatial directions in a position measurement system 100. The structures to be measured on the mask 102 are illuminated by illumination light, in which in the depicted exemplary embodiment, provision is made both for an illumination device 103 for transmitted illumination of the mask 102 and for an illumination device 104 for reflected illumination of the mask 102. Light coming from the mask 102 is imaged by an imaging optical unit 105 onto a detector unit 107 via a semitransparent mirror 106 and detected.

A control device 108 serves to control both the movement of the platform 101 supporting the mask 102 and the recording of the image data by the detector unit 107, and it is connected to an evaluation unit 109 in which the image data recorded by the detector unit 107 are evaluated for determining the position of the structures. To this end, the image data of the generated recordings are fed to the control device 108, from where the data are transmitted to the evaluation unit 109. The measurement image (in the form of a first aerial image) of a section of the mask 102, established by the position measurement system 100, can be compared to, e.g., a simulated second (aerial) image, whereupon the positioning error is then equated to the distance between the measurement image and the simulated image. In FIG. 1, "PP1" merely schematically indicates a pupil plane within the illumination device 103 and "PP2" indicates a pupil plane within the imaging optical unit 105.

In the following text, a method according to the invention is now described with reference to FIGS. 2 and 3. What a suitable calibration achieves in this method is that, taking into account the specifically measured structures in each case and the pupil illumination specifically used in the imaging optical unit of the position measurement system, the images to be compared (namely the measurement image and the simulated image) in the carried out image comparison (e.g., for establishing registration errors) also correspond in view of distortion effects, i.e., in other words, that structure-dependent and pupil illumination-dependent distortion effects or image aberrations can be correctly taken into account in each case.

Figure 2:
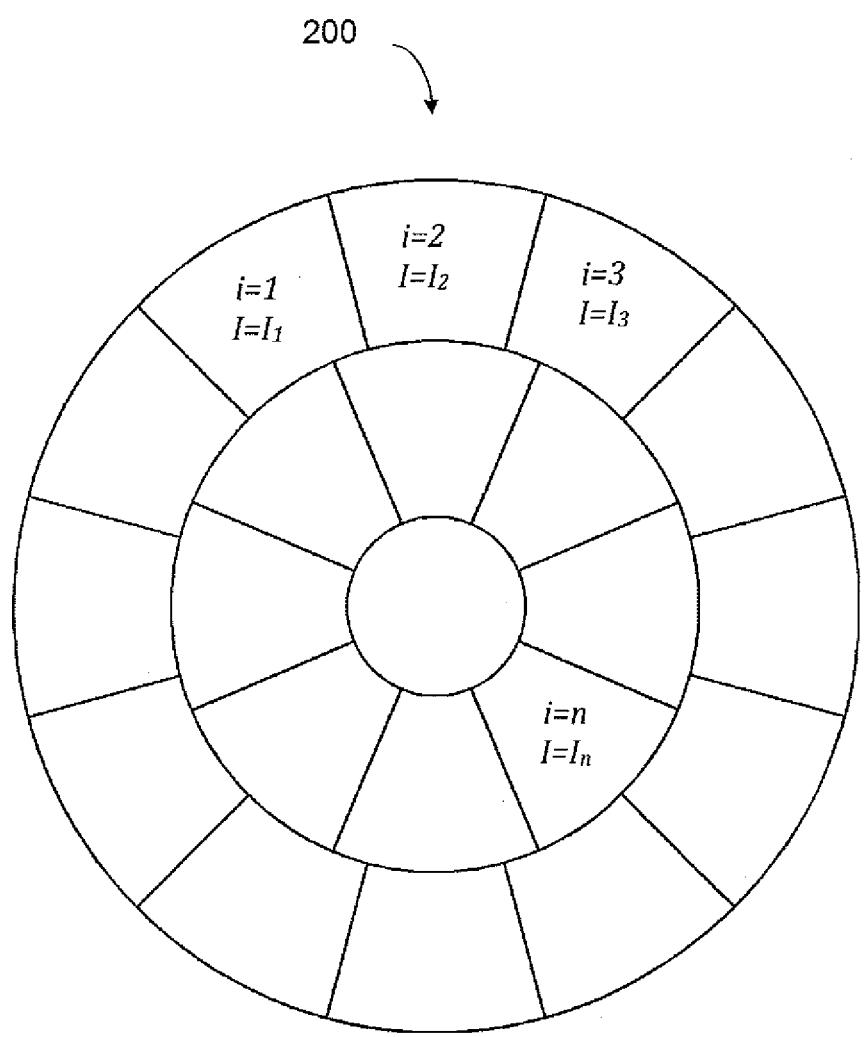
FIG. 2 shows a schematic illustration for explaining the concept underlying the present invention.

By way of illustration, FIG. 2 shows an exemplary decomposition or segmentation of an illumination pupil or of the pupil plane PP2 within the imaging optical unit 105 of the position measurement system 100 from FIG. 1, in which the number of segments (which is merely exemplary in FIG. 2 and, in principle, arbitrary) is denoted by "n" and in which "i" specifies the index of the respective segment. $I_i$ specifies the intensity obtained for the respective pupil illumination in the i-th segment.

Figure 3:
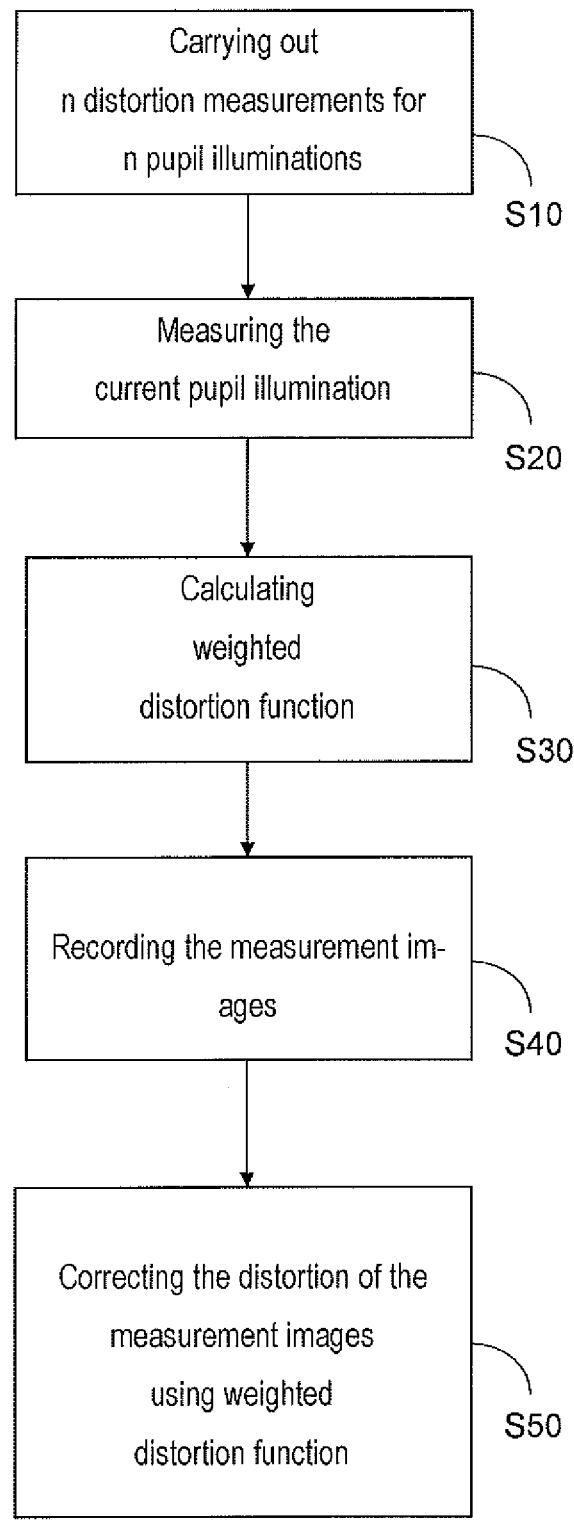
FIG. 3 shows a flowchart for explaining an embodiment of the method according to the invention.
Figure 4:
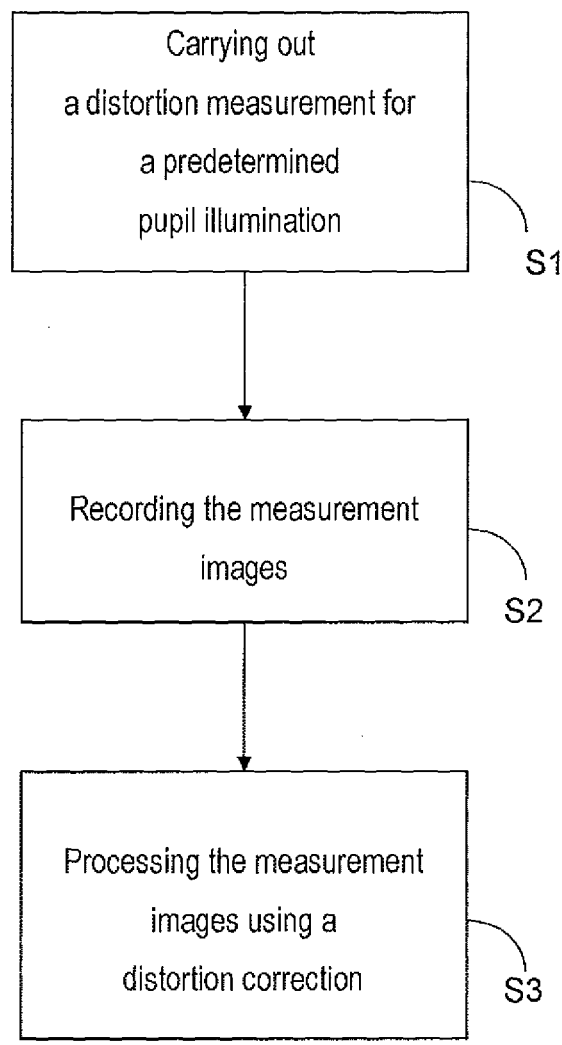
FIG. 4 shows a flowchart for explaining a conventional method.

Proceeding from the decomposition indicated in FIG. 2, FIG. 3 now shows a flowchart for explaining an embodiment of the method according to the invention.

In accordance with FIG. 3, a plurality (n) of distortion measurements are carried out in a first (calibration) step S10 in order to establish a plurality (n) of individual distortion functions $V_i(x, y)$, in which each of these individual distortion functions $V_i(x, y)$ in each case is assigned to a portion of the pupil plane PP2 within the imaging optical unit 105 from FIG. 1, that is to say, for example, to in each case one "pupil segment" in accordance with the exemplary decomposition of FIG. 2. The field coordinates, i.e., the coordinates in the image field of the imaging optical unit 105, are denoted by "x" and "y".

The method known per se from U.S. Pat. No. 8,416,412 B2 can be used for the calibration or for the carrying out of the aforementioned individual distortion measurements in step S10 (i.e., determining the individual distortion functions $V_i(x, y)$). Here, a test mask including a multiplicity of adjustment marks is arranged in different rotational or displacement positions and a measurement image is generated in each case, in which the positions for the respective adjustment marks obtained in the measurement image emerge from the position of the platform 101 supporting the mask, the position of the adjustment marks on the mask and the distortion (from which the respective distortion can be calculated).

Thereupon, in step S20, a pupil illumination, specifically used in the current measurement, within the imaging optical unit 105 of the position measurement system 100, i.e., a specific intensity distribution in the pupil plane PP2 in accordance with FIG. 1, is measured. Here, the associated intensity $I_i$ is determined for each "pupil segment" (e.g., in the exemplary decomposition of FIG. 2). The overall intensity in the pupil plane PP2 is $$I_{tot} = \sum_{i=1}^{n} I_i. \quad\text{(Equ. 1)}$$

Due to the currently used pupil illumination, a weighting factor $w_i$ can now be assigned to each segment in the pupil plane PP2, in which the following applies:

$$w_i = \frac{I_i}{I_{tot}}. \quad\text{(Equ. 2)}$$

In step S30, a weighted distortion function or overall distortion function $V_{tot}(x, y)$ is now calculated with the aid of the (n) individual distortion functions $V_i(x, y)$ established in step S10 and the currently used pupil illumination measured in step S20. The individual distortion functions $V_i(x, y)$ are included in this weighted distortion function or overall distortion function $V_{tot}(x, y)$ in accordance with the weighting factor applicable to the relevant pupil segment. In other words, each individual distortion function $V_i(x, y)$ is included in the overall distortion function $V_{tot}(x, y)$ to the extent to which the relevant "pupil segment" assigned to the respective individual distortion function contributes to the specifically used pupil illumination measured in step S20.

The overall distortion function $V_{tot}(x, y)$ now emerges from the individual distortion functions $V_i(x, y)$ (i.e., the distortion functions for the i segments) as $$V_{tot}(x, y) = \sum_{i=1}^{n} w_i \cdot V_i(x, y). \quad\text{(Equ. 3)}$$

In step S40, the measurement images are actually recorded by the detector unit 107 from FIG. 1. A distortion correction is then applied to these measurement images in step S50 by virtue of the image data recorded by the detector unit 107 being processed taking into account the weighted distortion function calculated in step S30.

When using the measurement images, corrected according to the invention, it is now possible, for example, to obtain increased accuracy in a subsequently carried out image comparison between a measurement image and a simulated image for establishing registration errors since, according to the invention, the pupil illumination specifically used in the imaging optical unit of the position measurement device is also taken into account, i.e., in other words, pupil illumination-dependent distortion effects or image aberrations were correctly taken into account.

Even though the invention has been described on the basis of specific embodiments, numerous variations and alternative embodiments are evident to a person skilled in the art, e.g., by combination and/or exchange of features of individual embodiments. Accordingly, it goes without saying for a person skilled in the art that such variations and alternative embodiments are concomitantly encompassed by the present invention, and the scope of the invention is defined by the accompanying patent claims and the equivalents thereof.

What is claimed is:

1. A method for establishing distortion properties of an optical system in a microlithographic measurement system, wherein the optical system has at least one pupil plane and wherein the distortion properties of the optical system are established on the basis of measuring at least one distortion pattern, which the optical system generates when imaging a predetermined structure in an image field,
    wherein the distortion properties of the optical system are established on the basis of a plurality of measurements of distortion patterns, wherein these measurements differ from one another in respect of the intensity distribution present in each case in the pupil plane,
    correcting at least one measurement image recorded by the optical system on the basis of the established distortion properties of the optical system, and
    establishing registration errors and/or structure widths on a mask using the corrected measurement image.

2. The method according to claim 1, wherein during the plurality of measurements of distortion patterns, only one segment from a plurality of segments is illuminated in each case in the pupil plane.

3. The method according to claim 1, wherein in a subsequently carried out image comparison between a measurement image and a simulated image, these images are aligned with respect to distortion effects on the basis of the established distortion properties of the optical system.

4. The method according to claim 1, comprising the following steps:
   a) establishing a distortion function ($V_i(x,y)$, $i=1, \ldots, n$)) in each case for a plurality of segments in the pupil plane, which distortion function specifies the distortion generated by the optical system in an image plane when illuminating the respective segment; and
   b) calculating an overall distortion function for a given intensity distribution in the pupil plane as $$V_{tot}(x, y) = \sum_{i=1}^{n} w_i \cdot V_i(x, y)$$

where $$w_i = \frac{I_i}{I_{tot}}$$

denotes a weighting factor assigned to the i-th segment in the pupil plane and $I_i$ denotes the intensity in the i-th segment for the given intensity distribution.

5. The method according to claim 1, wherein the measurement system comprises at least one of equipment for determining the position of structures on a microlithographic mask, an inspection measurement system for measuring defects of photomasks, equipment for determining the line width in photomasks, a phase measurement system for photomasks, or inspection equipment for localizing defects of photomasks.

6. The method according to claim 2, wherein at least one measurement image recorded by the optical system is corrected on the basis of the established distortion properties of the optical system.

7. The method according to claim 6, comprising the following steps:
   a) establishing a distortion function ($V_i(x,y)$, $i=1, \ldots, n$)) in each case for a plurality of segments in the pupil plane, which distortion function specifies the distortion generated by the optical system in an image plane when illuminating the respective segment; and
   b) calculating an overall distortion function for a given intensity distribution in the pupil plane as $$V_{tot}(x, y) = \sum_{i=1}^{n} w_i \cdot V_i(x, y)$$

where $$w_i = \frac{I_i}{I_{tot}}$$

denotes a weighting factor assigned to the i-th segment in the pupil plane and $I_i$ denotes the intensity in the i-th segment for the given intensity distribution.

8. The method according to claim 7, wherein the measurement system comprises at least one of equipment for determining the position of structures on a microlithographic mask, an inspection measurement system for measuring defects of photomasks, equipment for determining the line width in photomasks, a phase measurement system for photomasks, or inspection equipment for localizing defects of photomasks.

9. The method according to claim 6, wherein the measurement system comprises at least one of equipment for determining the position of structures on a microlithographic mask, an inspection measurement system for measuring defects of photomasks, equipment for determining the line width in photomasks, a phase measurement system for photomasks, or inspection equipment for localizing defects of photomasks.

10. The method according to claim 2, comprising the following steps:
   a) establishing a distortion function ($V_i(x,y)$, $i=1, \ldots, n$)) in each case for a plurality of segments in the pupil plane, which distortion function specifies the distortion generated by the optical system in an image plane when illuminating the respective segment; and
   b) calculating an overall distortion function for a given intensity distribution in the pupil plane as $$V_{tot}(x, y) = \sum_{i=1}^{n} w_i \cdot V_i(x, y)$$

where $$w_i = \frac{I_i}{I_{tot}}$$

denotes a weighting factor assigned to the i-th segment in the pupil plane and $I_i$ denotes the intensity in the i-th segment for the given intensity distribution.

11. The method according to claim 3, comprising the following steps:
   a) establishing a distortion function ($V_i(x,y)$, $i=1, \ldots, n$)) in each case for a plurality of segments in the pupil plane, which distortion function specifies the distortion generated by the optical system in an image plane when illuminating the respective segment; and
   b) calculating an overall distortion function for a given intensity distribution in the pupil plane as $$V_{tot}(x, y) = \sum_{i=1}^{n} w_i \cdot V_i(x, y)$$

where $$w_i = \frac{I_i}{I_{tot}}$$

denotes a weighting factor assigned to the i-th segment in the pupil plane and $I_i$ denotes the intensity in the i-th segment for the given intensity distribution.

12. The method according to claim 2, wherein the measurement system comprises at least one of equipment for determining the position of structures on a microlithographic mask, an inspection measurement system for measuring defects of photomasks, equipment for determining the line width in photomasks, a phase measurement system for photomasks, or inspection equipment for localizing defects of photomasks.

13. The method according to claim 3, wherein the measurement system comprises at least one of equipment for determining the position of structures on a microlithographic mask, an inspection measurement system for measuring defects of photomasks, equipment for determining the line width in photomasks, a phase measurement system for photomasks, or inspection equipment for localizing defects of photomasks.

14. The method according to claim 4, wherein the measurement system comprises at least one of equipment for determining the position of structures on a microlithographic mask, an inspection measurement system for measuring defects of photomasks, equipment for determining the line width in photomasks, a phase measurement system for photomasks, or inspection equipment for localizing defects of photomasks.

\* \* \* \* \*